Figure 1:
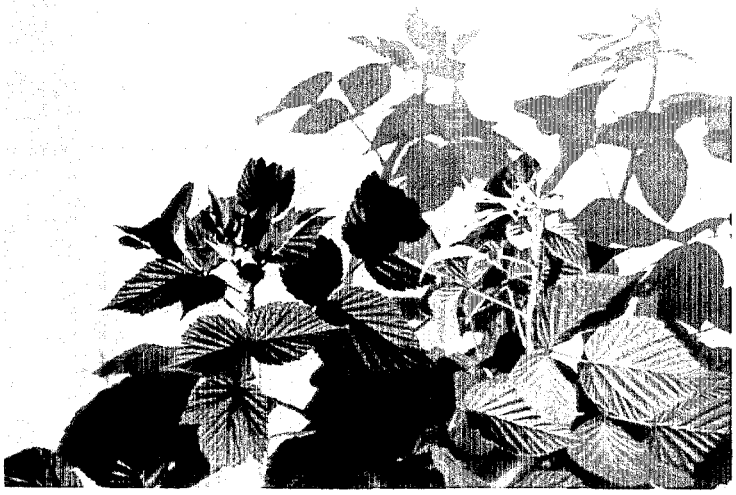

United States Patent [19]

Sanford et al.

[11] Patent Number: Plant 5,405

[45] Date of Patent: Feb. 12, 1985

[54] PURPLE RASPBERRY, N.Y. 632

[75] Inventors: John C. Sanford, Geneva; Donald K. Ourecky, Rochester, both of N.Y.; George L. Slate, deceased, late of Hilton, N.Y., by Barbara S. Abbott, heir

[73] Assignee: Cornell Research Foundation, Inc., Ithaca, N.Y.

[21] Appl. No.: 418,965

[22] Filed: Sep. 16, 1982

[51] Int. Cl.[3] ..... A01H 5/03

[52] U.S. Cl. ..... Plt./46

[58] Field of Search ..... Plt./46

*Primary Examiner*—Robert E. Bagwill

[57] ABSTRACT

A purple raspberry plant having good resistance to aphids and fruitworms, bearing large fruit of good quality.

8 Drawing Figures

SUMMARY

This invention is a new and distinct variety of summer-bearing purple raspberry which is exceptional for its large fruit, high yields, good fruit quality, and its multiple insect resistance.

ORIGIN

This new cultivar was developed by the Small Fruits Breeding Program of the Department of Pomology and Viticulture, Cornell University, New York State Agricultural Experiment Station, Geneva, N.Y. N.Y. 632 represents a purple raspberry backcrossed to a red raspberry, and is ¾ red raspberry and only 174 black rasperry. The cross was N.Y. 252 ('Cumberland'×'Newburgh') times N.Y. 17861 ('Newburgh'×'Indian Summer'), and was made in 1954. The specific clone was selected in 1957, and has been extensively tested under the number N.Y. 632. In the fall of 1982, N.Y. 632 will be named 'Royalty'.

DESCRIPTION

N.Y. 632 has vigorously growing and stout canes. The primocanes typically attain lengths of from about 150 cm to 240 cm, averaging about 195 cm, on soils of medium fertility. Primocane basal diameters range from about 9 mm to 21 mm, averaging about 14 mm. The primocanes and petioles are mostly purple with some green areas. The purple and green portions of the canes correspond approximately to the colors purple-violet 80B and green 145C on the color chart of The Royal Horticultural Society, London, England (all color numbers herein refer to said chart). During the dormant season, primocanes become a solid dark reddish purple (red-purple 59A). Spines are equally as numerous as in the cultivar 'Brandywine', but are substantially shorter and broader. Spines and the areas subtending the spines are dark purple. The base of the petiole is a darker purple than is surrounding tissue Foliage is rugose and distinctly bluish-green. Foliage has areas of purple pigmentation, especially on newly emerging foliage, on leaf margins, and on raised leaf surfaces. The primocanes are covered with a white waxy bloom. Newly established plantings have canes which need support, and tend to be prostrate. Mature plantings are more erect and tend to be self-supporting, except under very heavy crop loads. Plant habit and fruiting habit is like that characteristic of red rather than black raspberries. Propagation is by root suckers, which are relatively sparse. N.Y. 632 is also propagated effectively in vitro. Tip layering and node cuttings can also be effective, but tend to be somewhat difficult.

N.Y. 632 has late-maturing fruit which ripen in Geneva at the same times as Brandywine, in late July. The ripe fruit are attractive and extremely large. The first berries to ripen are conic shaped approximately twice as long as wide, while later fruit are smaller and round. Berry size ranges from approximately 17 mm×35 mm (6–8 grams in weight) down to 10×10 mm (2–3 grams). The median fruit size is approximately 12 mm×24 mm (4–6 grams). As the fruit develops, its color passes from white, to red, to purple, to deep purple (red purple—59B). Fully red berries will come free of the torus, are very firm, and have a mild red raspberry flavor, while purple fruit pick very easily and become progressively sweeter, softer, and accumulate more "purple" flavor. N.Y. 632 can be characterized as the only purple raspberry cultivar known to have single-gene immunity to *A. agathonica,* originating from 'Loyd George'. In addition, it has resistance to *A. rubicola* and *B. rubi.*

BRIEF DESCRIPTION OF PHOTOGRAPHS

The following are descriptions of the accompanying photographs, documenting the distinctive morphological features of this new cultivar.

FIG. 1—Terminal Primocane foliage of N.Y. 632 (left) is contrasted to terminal primocane foliage of the principle purple raspberry cultivar, Brandywine (right). Note the distinctly darker foliage of N.Y. 632, as well as the purple (vs. green) petioles, and purple (vs. green) coloration in the youngest leaflets of N.Y. 632.

Figure 2:
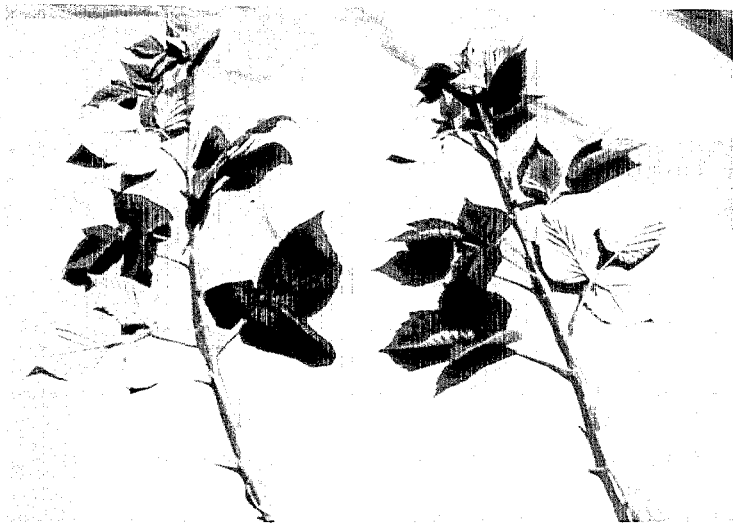

FIG. 2—Primocanes of N.Y. 632 (right) vs. Brandywine (left), with undersides of leaves, petioles, and stems displayed. Note that N.Y. 632 has slightly more rugose leaves, and has purple (vs. green) stem and petioles.

Figure 3:
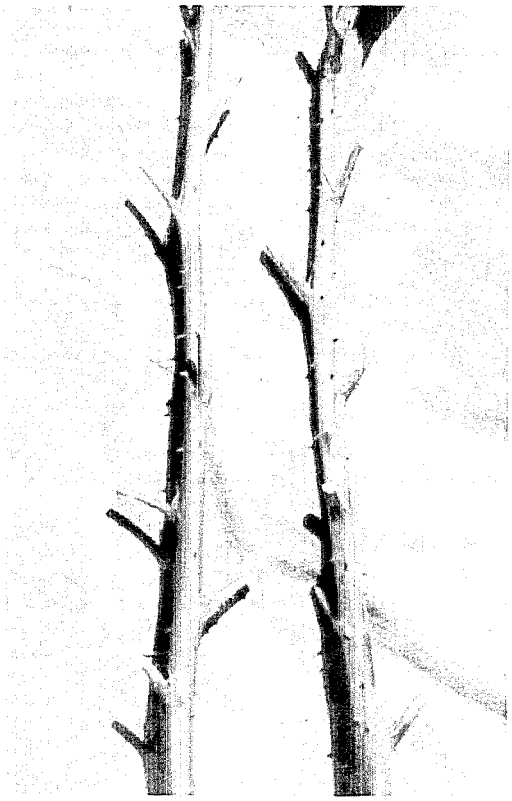

FIG. 3—Close-up of primocane stems of N.Y. 632 (right) and Brandywine (left). Note that N.Y. 632 has a blotchy purple stem. A waxy bloom covering the stem is also clearly visible on N.Y. 632, which has been wiped away where handled. The spines of N.Y. 632 are distinctly shorter and more squat than Brandywine, but are similar in number. The spines of N.Y. 632 are dark purple, in contrast to the green spines of Brandywine.

Figure 4:
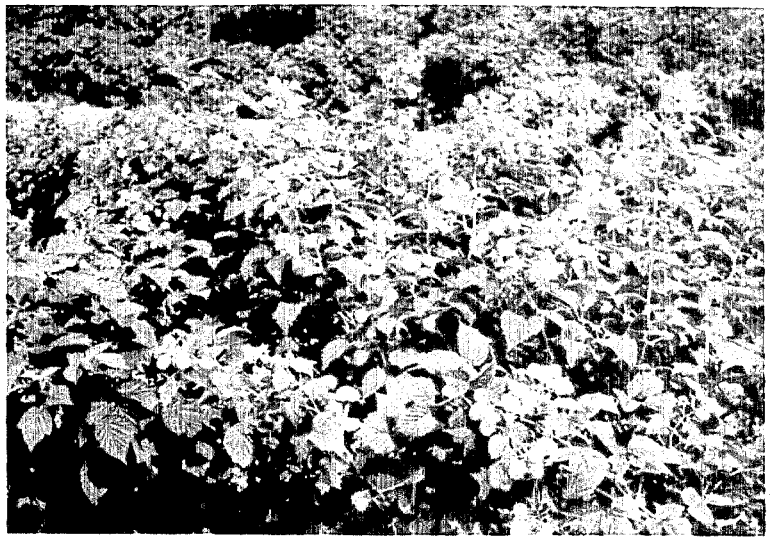

FIG. 4—A field planting of N.Y. 632 is shown. Note that N.Y. 632 has the plant habit of a red raspberry, producing root suckers resulting in a hedgerow rather than individual hills—unlike Brandywine. Note that N.Y. 632 can be heavily fruitful and erect.

Figure 5:
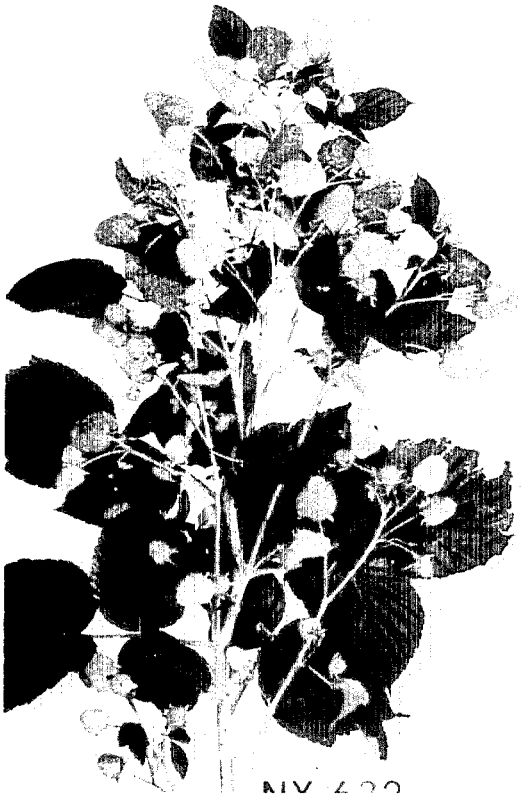

FIG. 5—Close-up of a fruiting cane of N.Y. 632. Note that the fruiting habit is a panicle like a red raspberry, rather than corymbose like a black raspberry. Also, note green, white, red and purple stages of fruit development. The long conic shape of the largest fruit can also be noted.

Figure 6:
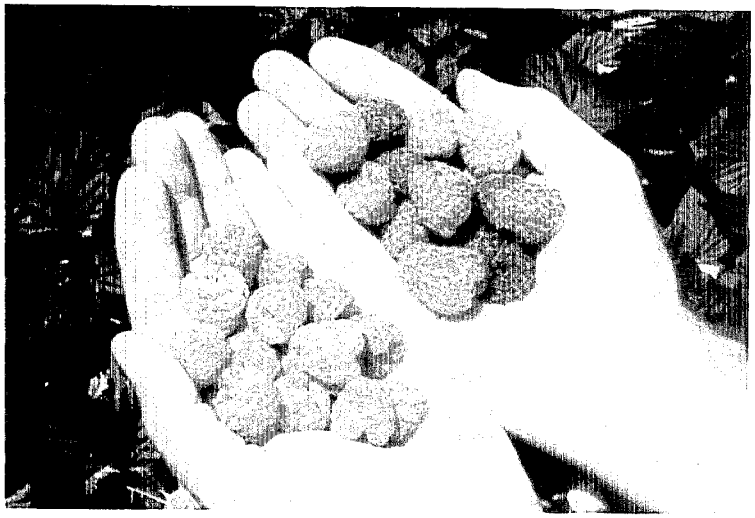

FIG. 6—Fruit of N.Y. 632. Note the large conic fruit. For scale, the lower berry, in the right hand, is 3.3 cm. long. N.Y. 632 is unique in having fruit which can easily be picked before physiological maturity. The left hand contains fruit which were picked at the red stage of fruit development. The berries remain coherent, and are very firm and are very suitable for shipping. Such fruit have an acceptable flavor, like that of a very mild red raspberry. The hand on the right contains berries which were picked at varying phases of purple fruit development. More mature berries become progressively softer, more succulent, sweeter, and develop more flavors characteristic of purple raspberries. Such berries are well suited for immediate consumption or processing.

Figure 7:
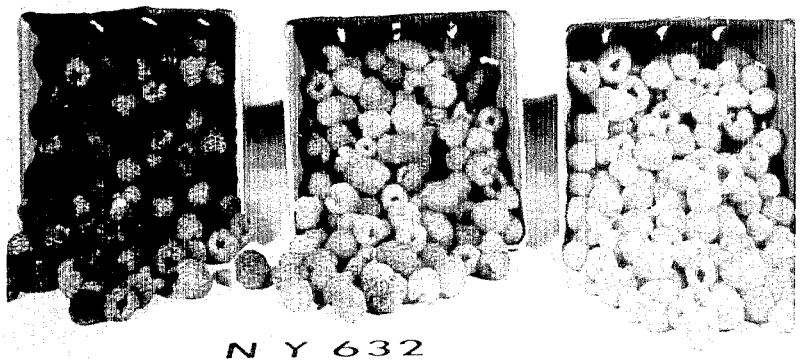

FIG. 7—Fruit of N.Y. 632 picked at the red, red-purple, and purple stages of fruit development.

Figure 8:
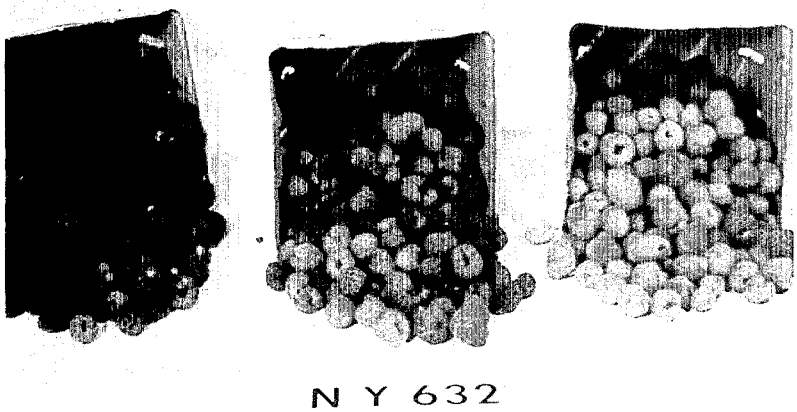

FIG. 8—The same berries are pictured in FIG. 7, but after one week of storage at 38° F.N.Y. 632 is unique in having the capacity to continue fruit maturation after picking. The fruit which were picked at the red stage have continued to mature and have become sweeter and softer, developing more purple flavor and the same red-purple color as berries picked at the red-purple stage. The fruit which was picked at the red-purple stage have developed into fully purple fruit with the same sweetness, flavor, texture and color as fresh purple berries. The fruit which was picked at the purple stage remains sweet and highly flavorful, but have become very soft and show some signs of breakdown.

MERITS

The most outstanding features of N.Y. 632 are its large fruit size, good fruit quality, insect resistance, yield potential, and its wide adaptation.

N.Y. 632 tends to be as large or larger than 'Hilton' and 'Brandywine', which are the largest fruited cultivars currently grown commercially in New York. Berries tend to weigh over 6 grams. Large fruit size greatly enhances the efficiency and speed of hand-picking, in addition to its visual appeal for the consumer.

Ripe fruit of N.Y. 632 are as sweet as most red raspberry fruit and are far sweeter than the fruit of 'Brandywine'. When fruit are picked at the full red stage, N.Y. 632 has a "mild" flavor characteristic of red raspberries. As the berries become darker they develop a fuller "purple" flavor characteristic of purple raspberries. This flavor is not accompanied by the sour, highly acid, or "soapy" flavors which are sometimes encountered in purple raspberries. N.Y. 632 produces outstanding jelly or jam which is comparable with that of 'Brandywine'.

N.Y. 632 is unusual in having triple insect resistance. It is immune to the large-bodied raspberry aphid, *A. agathonica,* which helps it to escape infection by the mosaic viruses, since these viruses are only transmitted by this aphid (1). N.Y. 632 is also highly resistant to the small-bodied raspberry aphid, *A. rubicola,* (being most resistant of 21 raspberry clones tested) which should help it to escape raspberry leaf curl virus (2). These two aphid resistances, will help N.Y. 632 to escape the principle lethal raspberry viruses in the eastern United States.

The adult of the raspberry fruitworm, *B. rubi,* causes its most severe damage to young buds. Later the larvae can damage developing fruit and can contaminate mature fruit. N.Y. 632 has been shown to be highly resistant to adult fruitworm bud damage, having the highest level of resistance among 23 clones tested (3). N.Y. 632 was also found to be among the most resistant raspberries tested, when evaluated for larval damage occurring later in fruit development.

N.Y. 632 has considerable hardiness, good yield potential and wide adaptation. Nine of eleven cooperative testers surveyed ranked N.Y. 632 as 'superior' or 'outstanding' relative to yield and hardiness. Favorable reports from field evaluations have come from Washington, Kansas, Iowa, Ohio and Ontario (Canada), as well as from New York State.

N.Y. 632 is soft and juicy when fully ripe. As such, it has appeal for pick-your-own customers, but would be poorly suited for shipping or wholesale marketing. However, when N.Y. 632 is picked at the full-red stage of fruit development, it has already reached a very acceptable level of quality, relative to sugar content, flavor, and appearance. At this stage the fruit are very firm and solid, and have an extended shelf life. Such fruit continue to ripen after picking, and become sweeter and develop more purple color and flavor in storage. Therefore, N.Y. 632 seems to simultaneously offer the pick-your-own customer a large sweet, and succulent purple berry; while offering the wholesale or retail market a firm red berry with acceptable quality and a reasonable shelf life.

We claim:

1. The new and distinct variety of raspberry herein described and illustrated and identified by the characters enumerated above.

* * * * *

UNITED STATES PATENT AND TRADEMARK OFFICE

CERTIFICATE OF CORRECTION

PATENT NO. : Plant Patent No. 5,405

DATED : February 12, 1985

INVENTOR(S) : SANFORD ET AL.

It is certified that error appears in the above—identified patent and that said Letters Patent is hereby corrected as shown below:

Page 1, column 1, line 12, "174 should read --1/4--;

Page 1, column 1, line 36, after "tissue", please insert a period --.--.

Signed and Sealed this

*Sixteenth* Day of *July 1985*

[SEAL]

*Attest:*

DONALD J. QUIGG

*Attesting Officer* *Acting Commissioner of Patents and Trademarks*